United States Patent
Arrowood et al.

(10) Patent No.: US 9,328,080 B2
(45) Date of Patent: May 3, 2016

(54) PREPARATION OF DIHYDROXYETHYL PIPERAZINE

(71) Applicant: Dow Global Technologies LLC, Midland, MI (US)

(72) Inventors: Tina L. Arrowood, Elko New Market, MN (US); Jason C. MacDonald, Bay City, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/424,842

(22) PCT Filed: Sep. 4, 2013

(86) PCT No.: PCT/US2013/058054
§ 371 (c)(1),
(2) Date: Feb. 27, 2015

(87) PCT Pub. No.: WO2014/039551
PCT Pub. Date: Mar. 13, 2014

(65) Prior Publication Data
US 2015/0274682 A1    Oct. 1, 2015

Related U.S. Application Data

(60) Provisional application No. 61/697,094, filed on Sep. 5, 2012.

(51) Int. Cl.
*C07D 241/04* (2006.01)
*C07D 295/04* (2006.01)
*C07D 295/088* (2006.01)
*B01J 27/232* (2006.01)
*B01J 31/02* (2006.01)
*B01J 31/16* (2006.01)

(52) U.S. Cl.
CPC ........... *C07D 295/088* (2013.01); *B01J 27/232* (2013.01); *B01J 31/0225* (2013.01); *B01J 31/0244* (2013.01); *B01J 31/16* (2013.01); *C07D 241/04* (2013.01); *C07D 295/04* (2013.01); *Y02P 20/582* (2015.11)

(58) Field of Classification Search
CPC . C07D 241/04; C07D 295/04; C07D 295/088
See application file for complete search history.

(56) References Cited

U.S. PATENT DOCUMENTS 5,491,263 A    2/1996  Rooney
2012/0108816 A1* 5/2012  Wigbers ............ C07D 295/088
                                                544/401

OTHER PUBLICATIONS

PCT/ISA/210, WO, International Search Report.
Jiri Trejbal et al: "Kinetics of ethylenediamine and piperazine ethoxylation", Reaction Kinetics and Catalysis Letters, Springer Science+Business Media, Dordrecht, NL, vol. 82, No. 2, Jul. 1, 2004, pp. 339-346, XP019265226, ISSN 1588-2837.

* cited by examiner

*Primary Examiner* — Erich A Leeser
(74) *Attorney, Agent, or Firm* — Akerman LLP

(57) ABSTRACT

A process for selectively preparing dihydroxyethyl piperazine by reacting hydroxyethyloxazolidinone with an acid catalyst wherein the selectivity of hydroxyethyloxazolidinone to dihydroxyethyl piperazine is at least 55%.

14 Claims, No Drawings

PREPARATION OF DIHYDROXYETHYL PIPERAZINE

FIELD OF INVENTION

The invention generally relates to dihydroxyethyl piperazine and processes for the synthesis of the same. More specifically, the invention relates to methods for synthesis of dihydroxyethyl piperazine from hydroxyethyloxazolidinone under catalytic conditions, resulting in the selective formation of dihydroxyethyl piperazine.

BACKGROUND OF THE INVENTION

Piperazine compounds have any number of practical applications including the production of plastics, resins and other industrial work products. Piperazines may also be used in various end use applications such as in pesticides, automotive fluids and in pharmaceuticals.

One clear application for piperazine compounds is in the absorption of various contaminants often found resident in oil and gas streams. In specific, piperazine compounds and derivatives thereof such as N-alkyl-N-hydroxyethylpiperazine, N-hydroxyethylpiperazine and N,N-di(2-hydroxyethyl) piperazine (herein referred to as dihydroxyethyl piperazine or DiHEP) have been found useful due to their affinity for absorbing sulfur compounds and their ready reclamation for reuse in the absorption process (see, U.S. Pat. No. 5,098,681).

Generally, dihydroxyethyl piperazine is commercially available through processes such as, for example, the ethoxylation of piperazine (Gold-Aubert, Ph et. al. *Helvetica Chimica Acta* 1959, 42, 1156; Trejbal, Jiri, et. al. *Reaction Kinetics and Catalysis Letters* 2004, 82(2), 339), and the reductive alkylation and cyclization reaction of amino ethanolamine and diethanoamine in the presence of a hydrogen atmosphere and a hydrogenation dehydrogenation catalyst (see, U.S. Pat. No. 4,338,443).

Further, Rooney, U.S. Pat. No. 5,491,263 also discloses a method for the production of substituted ethylene diamines by reacting oxazolidinone with secondary amines or alkyl aryl amines.

One concern with these processes is that they generally produce a mixture of piperazine compounds along with the dihydroxyethyl piperazine. It is not uncommon for the ethoxylation process to produce piperazine, hydroxyethyl piperazine, and dihydroxy ethyl piperazine in mixture; among other compounds. This has been documented by others; Trejbal et al, Kinetics of Ethylenediamine and Piperazine Ethoxylation, Reaction Kinetics and Catalysis Letters (2004), 82(2) at 339-346 discusses the ethoxylation of ethylene diamine and piperazine.

Additionally, the selectivity of the processes described above suffers. Thus side products generated by these processes must be useful as a mixture or require the addition of extensive processing steps to purify the dihydroxyethyl piperazine must be applied.

Even still, there are many instances where dihydroxyethyl piperazine is preferred as more useful than a mixture of piperazine compounds. As such, there is a need for a process, and resulting composition, which produces dihydroxyethyl piperazine in an efficient commercially viable manner at a high level of purity.

SUMMARY OF THE INVENTION

In accordance with a first aspect of the invention, there is provided a process for selectively preparing dihydroxyethyl piperazine by reacting N-(2-hydroxyethyl) oxazolidinone with an acid catalyst wherein the selectivity of —N-(2-hydroxyethyl) oxazolidinone to dihydroxyethyl piperazine is at least 55% pure.

In accordance with a further aspect of the invention, there is provided a synthetic dihydroxyethyl piperazine produced by a catalytic reaction, the said catalyst comprising a triflate compound, wherein the dihydroxyethyl piperazine as present in mixture, is at least about 55 wt-% pure.

The invention is a process and resulting product, for producing dihydroxyethyl piperazine. The process of the invention comprises the selective conversion of an N-(2-hydroxyethyl) oxazolidinone (HEO) to dihydroxyethyl piperazine (DiHEP). The process is implemented using acid catalysts.

While only theory, it is believed that in the presence of an acid catalyst, N-(2-hydroxyethyl) oxazolidinone exists as an equilibrium mixture of N-(2-hydroxyethyl) oxazolidinone, diethanolamine and carbon dioxide. The diethanolamine will react with N-(2-hydroxyethyl) oxazolidinone to form trishydroxyethyl ethylenediamine which undergoes acid catalyzed dehydration to form the dihydroxyethyl piperazine.

In accordance with the invention it has been found that the presence of a tertiary nitrogen atom in the amine compound is especially useful in absorbing acid gases such as $CO_2$, $SO_2$, $H_2S$, etc found as contaminants common to many of the gases derived from natural sources.

DETAILED DESCRIPTION OF THE PREFERRED EMBODIMENTS

In accordance with one aspect, the invention is a process for selectively preparing dihydroxyethyl piperazine by reacting N-(2-hydroxyethyl) oxazolidinone with an acid catalyst wherein the selectivity of N-(2-hydroxyethyl) oxazolidinone to dihydroxyethyl piperazine is preferably at least 55% pure.

The invention is a process of producing dihydroxyethyl piperazine through synthetic method. Generally dihydroxyethyl piperazine has the formula:

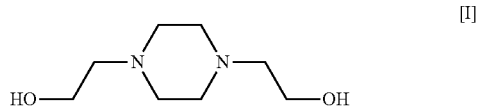 [SMILES: OCCN1CCN(CCO)CC1]

The method of the invention comprises converting N-(2-hydroxyethyl) oxazolidinone (II) through catalytic reaction to dihydroxyethyl piperazine.

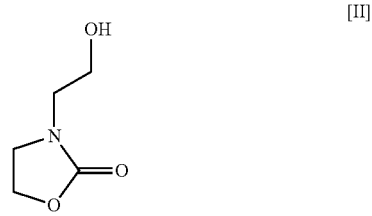

As part of the process of the invention, N-(2-hydroxyethyl) oxazolidinone is treated with a catalyst suitable to both ring open the structure and couple two N-(2-hydroxyethyl) oxazolidinone molecules together and promote dehydration in the reaction to form the piperazine ring structure. Any catalyst which can promote the coupling and dehydration reactions may be used in accordance with the invention.

Preferably the catalyst is chosen from a group comprising Lewis acid catalysts and Bronsted acid catalysts. Lewis acid catalysts have been found especially useful in facilitating both the coupling and dehydration reactions toward the synthesis of the dihydroxyethyl piperazine.

Lewis acids are defined as any compound which can accept an electron lone pair from another molecule. Examples of Lewis acids that can be used include: metal halides such as boron trihalides and complexes thereof, aluminum trihalides, and antimony pentahalide; Group 2-15 metal ligand complexes such as metal triflate, metal tosylate, metal seen complexes, metal salphen complexes; tris-perfluoronated aryl borate; quarternary ammonium compounds and combinations thereof. An example of a metal triflate that can be used is aluminum triflate.

Particularly useful catalysts include triflate compounds such as yttrium triflate ($Y(CF_3SO_3)_3$), aluminum triflate ($Al(CF_3SO_3)_3$), zinc triflate ($Zn(CF_3SO_3)_2$), lanthanum triflate ($La((CF_3SO_3)_3$) and mixtures thereof. Also useful as a catalyst, either alone or with any of the triflate compounds previously referenced are bronsted acids such as, for example, 3-nitro-benzenesulfonic acid, para-toluene sulfonic acid, benzenesulfonic acid, triflic acid, sulfuric acid, phosphoric acid, hydrochloric acid, and carboxylic acids (e.g., acetic acid, benzoic acid, citric acid).

The acid catalysts may also be used as a homogeneous catalyst or bound to a support as a heterogeneous catalyst.

Generally, the N-(2-hydroxyethyl) oxazolidinone may be selectively converted to dihydroxyethyl piperazine over an acid catalyst under ambient conditions. Although it has been found that conditions of increased temperature reduce the time required.

General process parameters such as catalyst type, catalyst concentration, reaction temperature, addition of a solvent, and % conversion can each independently or in combination be optimized to achieve the most selective and/or economical process.

A summary of reaction conditions may be found in the table below.

TABLE

|  | Useful | Preferred | More Preferred |
| --- | --- | --- | --- |
| Time | <48 h | <24 h | <8 h |
| Temperature | <120 C. | <180 C. | <250 C. |
| Catalyst Concentration | <20 mol % | <10 mol % | <1 mol % |

While one of skill in the art having read this specification will understand that the dihydroxyethyl piperazine produced through the method of the invention is generally produced in mixtures at yields ranging from at least about 55 wt-%, preferably at least about 80 wt-%, and more preferably about 90 wt-%. The actual yield will depend upon catalyst and relevant reaction conditions. The yield of dihydroxyethyl piperazine is based upon the moles of N-(2-hydroxyethyl) oxazolidinone reacted. It is typical under process implementation to balance conversion with product selectivity through the implementation of reactant recycle operations. The ratio of reactant to product selectivity is very important in this instance. Having high reactant conversion in addition to high product selectivity is most preferred as this reduces the amount of product recycle or enables one to use the product without further purification. Yttrium triflate and aluminum triflate are preferred. Additionally, providing a means to remove the evolving carbon dioxide byproduct is preferred to achieve the most desired yield and product selectivity.

We have found that N-(2-hydroxyethyl) oxazolidinone undergoes a catalytic coupling reaction followed by catalytic dehydration which, in turn, results in the synthesis of dihydroxyethyl piperazine.

Working Examples

The following examples provide a nonlimiting illustrative depiction of one embodiment of the invention:
Hydroxyethyloxazolidinone (HEO)

N-(2-hydroxyethyl) oxazolidinone is a known chemical and is available in research quantities from Pfaulz and Bauer. The most common synthetic methods involve the reaction of diethanolamine (DEA) with dialkylcarbonates generating an alcohol by-product. This reaction proceeds without a catalyst but can be promoted with a sodium alkoxide. HEO is also reported as a product from the reaction of diethanolamine (DEA) and carbon dioxide (Scheme III below). Under these conditions, however, the HEO intermediate is short lived and condenses with additional DEA to form tris(2-hydroxyethyl) ethylenediamine (TriHEED).

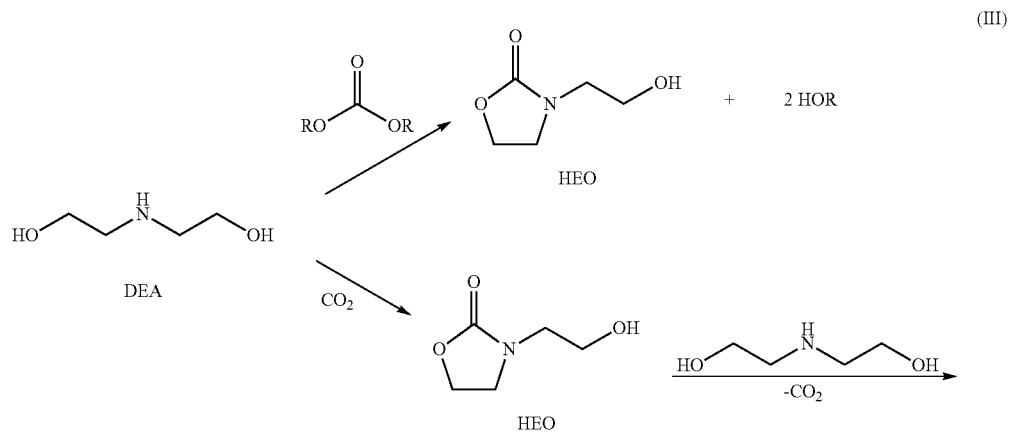

(III)

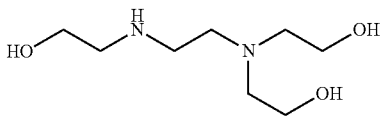
TriHEED

HEO is stable in the absence of catalyst up to 200° C. The reactivity of HEO with itself was evaluated when heated at 180° C. with 5 mol % of various catalysts. The resulting reaction mixture was evaluated after 25 hours by $^1$H NMR to determine the conversion of HEO and selectivity of the product mixture to dihydroxyethyl piperazine.

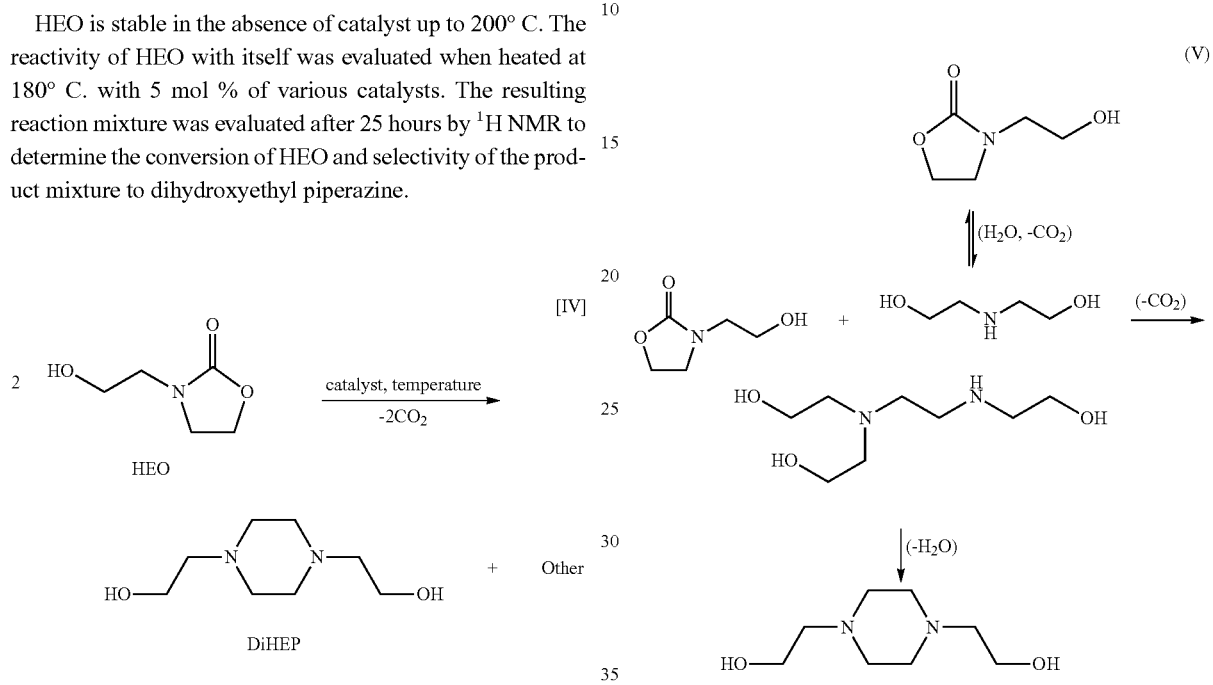

Reaction occurred with all the catalysts employed. The base catalysts (potassium carbonate, 1,5-diazabiocyclo[4.3.0]non-5-ene (DBN)) are more active than Lewis metal triflate catalysts such as: ($Y(OTf)_3$, $Al(OTf)_3$, $La(OTf)_3$, $Zn(OTf)_2$) or Bronsted acids (p-toluenesulfonic acid (PTSA)). $^1$H NMR analysis of final reaction mixtures of the base catalyzed reactions show new broad peaks at 2.6 and 3.6 ppm indicative of polymeric materials with C—H functionality adjacent to an amine and/or ether moeity (i.e., polyether and/or polyamines). The Lewis acid catalyzed reaction mixtures do not react significantly until after 10 hours of heating. The final reaction mixtures have sharp peaks in the proton NMR indicating the products are mainly non-polymeric materials.

The products from the various screening conditions were examined by GCMS, LCMS and $^1$H and $^{13}$C NMR. This confirmed that the product composition of the acid catalyzed reactions ($Al(OTf)_3$, $Zn(OTf)_2$, $Y(OTf)_3$, p-toluenesulfonic acid) comprise small molecules with the main product being dihydroxyethylpiperazine (DiHEP). DiHEP is the intramolecular condensation and thermodynamically favored product from TriHEED. This path is favored under acid conditions since the catalyst promotes the interamoleculear cyclization of TriHEED and reduces products from the reaction of TriHEED with additional HEO (Scheme V, below).

EXPERIMENTAL

Catalyzed reaction of HEO: Under ambient conditions, catalyst (1.9 mmol; 5 mole %) and N-(2-hydroxyethyl)oxazolidinone (0.50 g, 38 mmol) were added to a 5 ml thick-walled Wheaton V-vial and capped using a red rubber septum screw cap. The vial was vented using a 18 gauge needle through the septum and the mixture was stirred and heated at 180° C. for 25 h. The conversion and selectivity was measured using $^1$H NMR analysis of the reaction mixture after 25 hours and is summarized in Table 1.

TABLE 1

| | | 25 h reaction composition (mol fraction) | | | HEO % conversion | DiHEP % product selectivity |
|---|---|---|---|---|---|---|
| entry | Catalyst | HEO | DiHEP | Other | | |
| 1-1 | No Catalyst | 0.89 | 0.065 | 0.045 | 11.0 | 59.1 |
| 1-2 | $K_2CO_3$ | 0.06 | N/A[1] | N/A[1] | 94.0 | Trace[2] |
| 1-3 | DBN | 0.08 | N/A[1] | N/A[1] | 92.3 | Trace[2] |
| 1-4 | $Y(OTf)_3$ | 0.03 | 0.79 | 0.18 | 97.2 | 81.2 |
| 1-5 | PTSA | 0.55 | 0.25 | 0.19 | 44.6 | 56.9 |
| 1-6 | $Zn(OTf)_3$ | 0.36 | 0.41 | 0.23 | 63.9 | 63.8 |
| 1-7 | $Al(OTf)_3$ | 0.10 | 0.62 | 0.27 | 89.7 | 69.4 |
| 1-8 | $La(OTf)_3$ | 0.25 | N/A[1] | N/A[1] | 75.2 | Moderate[3] |

[1] A value could not be determined due to the signal interference of polymeric by-products.
[2] Trace levels of DiHEP was observed in the material which could be dissolved and evaluated by GC/MS
[3] Due to the signal interference of the polymeric by-products, a selectivity number could not be determined; however, the relative abundance of the DiHEP observed by GC/MS was significantly higher than with entries 1-2 and 1-3.

The mole fraction of the components in the 25 hour reaction mixture was determined by integrating all the peaks in the $^1$H NMR and normalizing to 100. The integration of the HEO peak at 4.4 ppm (a CH$_2$ group of the hydroxyethyl functionality) and the DiHEP peak at 3.6 ppm (a CH$_2$ group of the hydroxyethyl functionality; there are two equivalent hydroxyethyl functionalities in DiHEP, thus the CH$_2$ group integration represents a sum of both of these functional groups, i.e. 4 protons) were used to measure the mole fraction of these species in the product mixture. Example calculation for HEO mole fraction in the product: (integration of CH$_2$ peak of HEO at 4.4 ppm/2 hydrogens)=integration/1 hydrogen in HEO; (integration/1 hydrogen)×(9 hydrogen)=total integration from all hydrogens of HEO. The total integration from all hydrogen is divided by 100 to provide the mole fraction of the HEO in the product mixture. Example calculation for DiHEP mole fraction in the product: (integration of CH$_2$ peak of DiHEP at 3.6 ppm)/(4 hydrogen)=integration/1 hydrogen in DiHEP; (integration/1 hydrogen)×(18 hydrogen)=total integration from all hydrogen of DiHEP. The total integration from all hydrogen is divided by 100 to provide the mole fraction of HEO in the product mixture. The mole fraction of HEO and DiHEP is subtracted from 1 to provide the mole fraction of any other remaining material.

HEO % conversion is determined by subtracting the mole fraction of the HEO observed in the product from 1 and multiplying by 100. DiHEP % selectivity is determined by dividing the DiHEP mole fraction by the sum of DiHEP mole fraction and "other" product mole fraction, then multiplying by 100.

Although the present invention has been described by reference to its preferred embodiment as is disclosed in the specification and drawings above, many more embodiments of the present invention are possible without departing from the invention. Thus, the scope of the invention should be limited only by the appended claims.

The claimed invention is:

1. A method for the synthesis of dihydroxyethyl piperazine comprising the step of:

converting N-(2-hydroxyethyl) oxazolidinone to dihydroxyethyl piperazine through exposure to an acid catalyst.

2. The method of claim 1 wherein the selectivity of N-(2-hydroxyethyl) oxazolidinone to dihydroxyethyl piperazine is at least 55%.

3. The method of claim 1, wherein said acid catalyst comprises a Lewis acid.

4. The method of claim 3, wherein said acid catalyst comprises a triflate compound.

5. The method of claim 4, wherein said triflate compound is selected from the group consisting of Yttrium triflate, Zinc triflate, Aluminum triflate, Lanthanum triflate, and mixtures thereof.

6. The method of claim 4, wherein said acid catalyst comprises Yttrium triflate.

7. The method of claim 1, wherein said acid catalyst comprises a Bronsted acid.

8. The method of claim 7, wherein said acid catalyst comprises para-toluene sulfonic acid.

9. The method of claim 1, wherein said acid catalyst is bound to a support.

10. The method of claim 1, wherein said N-(2-hydroxyethyl) oxazolidinone is converted to said dihydroxy ethyl piperazine by exposure to a triflate catalyst at temperatures ranging up to about 120° C. for a time ranging up to about 48 hours.

11. The method of claim 1, wherein said acid catalyst comprises Yttrium triflate, and said N-(2-hydroxyethyl) oxazolidinone is exposed to said catalyst at a temperature ranging up to 250° C., for a time ranging up to about 8 hours.

12. The method of claim 2, wherein said acid catalyst comprises a Lewis acid.

13. The method of claim 12, wherein said Lewis acid comprises a triflate compound and said triflate compound is selected from the group consisting of Yttrium triflate, Zinc triflate, Aluminum triflate, Lanthanum triflate, and mixtures thereof.

14. The method of claim 12, wherein said Lewis acid comprises Yttrium triflate.

* * * * *